(12) United States Patent
Sughrue et al.

(10) Patent No.: US 12,159,333 B2
(45) Date of Patent: Dec. 3, 2024

(54) VISUALIZATION OF COMPLEX CONNECTOME INTERACTIONS

(71) Applicant: Omniscient Neurotechnology Pty Limited, Sydney (AU)

(72) Inventors: Michael Edward Sughrue, Brighton Le Sands (AU); Stephane Philippe Doyen, Mount Kuring Gai (AU); Onur Tanglay, Mortlake (AU); Xinling Jiang, Willoughby (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 319 days.

(21) Appl. No.: 17/739,042

(22) Filed: May 6, 2022

(65) Prior Publication Data

US 2023/0360293 A1 Nov. 9, 2023

(51) Int. Cl.
*G06T 11/20* (2006.01)
*A61B 5/00* (2006.01)
*G06T 7/00* (2017.01)
*G16H 30/40* (2018.01)
*G16H 50/20* (2018.01)
(Continued)

(52) U.S. Cl.
CPC .......... *G06T 11/206* (2013.01); *A61B 5/4064* (2013.01); *A61B 5/7267* (2013.01); *A61B 5/7275* (2013.01); *A61B 5/742* (2013.01); *G06T 7/0012* (2013.01); *G16H 30/40* (2018.01); *G16H 50/20* (2018.01); *G16H 50/50* (2018.01); *G16H 50/70* (2018.01); *G06T 2200/24* (2013.01); *G06T 2207/20072* (2013.01);
(Continued)

(58) Field of Classification Search
None
See application file for complete search history.

(56) References Cited

U.S. PATENT DOCUMENTS

2012/0271148 A1* 10/2012 Nelson ............... A61N 1/36139
                                                                600/407
2016/0019693 A1*  1/2016 Silbersweig ............ G06T 11/60
                                                                382/128
(Continued)

OTHER PUBLICATIONS

Akiki et al., "Determining the Hierarchical Architecture of the Human Brain Using Subject-Level Clustering of Functional Networks," Sci Rep, Dec. 17, 2019, 15 pages.
(Continued)

*Primary Examiner* — James A Thompson
*Assistant Examiner* — Kim Thanh T Tran
(74) *Attorney, Agent, or Firm* — Fish & Richardson P.C.

(57) ABSTRACT

Methods, systems, and apparatus, including computer programs encoded on computer storage media, for visualizing complex connectome interactions relevant to a medical condition. One of the methods includes receiving brain data for a brain of a patient, processing the brain data to determine multiple brain parcels that are predicted to be relevant to a medical condition, determining, for each of multiple brain parcels that are predicted to be relevant to the medical condition, a respective brain network affiliation, and providing, to a user device of a user, data for displaying a visualization that includes one or more respective brain network affiliations determined for each of multiple brain parcels that are predicted to be relevant to the medical condition.

14 Claims, 8 Drawing Sheets

EXAMPLE PROCESS FOR VISUALIZING COMPLEX CONNECTOME INTERACTIONS

(51) Int. Cl.
   *G16H 50/50*   (2018.01)
   *G16H 50/70*   (2018.01)
(52) U.S. Cl.
   CPC .............. *G06T 2207/20081* (2013.01); *G06T 2207/30016* (2013.01); *G06T 2210/41* (2013.01)

(56) References Cited

U.S. PATENT DOCUMENTS

2021/0005306 A1\* 1/2021 Anticevic .............. G16H 20/70
2022/0399117 A1\* 12/2022 Leuthardt .............. G16H 50/20

OTHER PUBLICATIONS

Doyen et al., "Hollow-tree Super: a directional and scalable approach for feature importance in boosted tree models," Oct. 25, 2021, 28 pages.
Lundberg et al., "A Unified Approach to Interpreting Model Predictions," 31st Conference on Neural Information Processing Systems, 2017, 10 pages.
Ribeiro et al., "Why should I trust you: explaining the prediction of of any classifer," Proceedings of the 22nd ACM SIGKDD International Conference on Knowledge Discovery and Data Mining, 2016, 1135-1144.

\* cited by examiner

EXAMPLE BRAIN NETWORK AFFILIATIONS 400

VISUALIZATION OF COMPLEX CONNECTOME INTERACTIONS

TECHNICAL FIELD

The present disclosure generally relates to using machine learning on medical imaging data.

BACKGROUND

Medical imaging includes the technique and process of creating visual representations of the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging also establishes a database of normal anatomy and physiology.

SUMMARY

This specification describes a method for generating a visualization of brain network affiliations of different regions of the brain of a patient that are predicted to contribute to a symptom, a medical condition, a behavior, or a trait. The method includes receiving brain data for a brain of a patient, processing the brain data to determine multiple brain parcels that contribute to a medical condition, determining a respective brain network affiliation of each brain parcel, and forwarding data for displaying a visualization that includes one or more respective brain network affiliations determined for the medical condition.

According to a first aspect, there is provided a method that includes: receiving brain data for a brain of a patient, processing the brain data to determine multiple brain parcels that are predicted to be relevant to a medical condition, determining, for each of the brain parcels that are predicted to be relevant to the medical condition, a respective brain network affiliation, and providing, to a user device of a user, data for displaying a visualization that includes one or more respective brain network affiliations determined for each of the brain parcels that are predicted to be relevant to the medical condition.

In some implementations, the respective brain network affiliation specifies a brain network of multiple brain networks of the brain of the patient that have been identified using a hierarchical clustering algorithm.

In some implementations, the method further includes receiving brain data for multiple patients.

In some implementations, the method further includes taking an action based on the visualization that includes one or more respective brain network affiliations determined for each of multiple brain parcels that are predicted to be relevant to the medical condition.

In some implementations, taking the action based on the visualization that includes one or more respective brain network affiliations determined for each of multiple brain parcels that are predicted to be relevant to the medical condition includes: exporting data identifying the one or more respective brain network affiliations for the medical condition.

In some implementations, the method further includes receiving a selection of the medical condition.

In some implementations, the visualization further includes a selection of the medical condition and an indication of multiple brain parcels that are predicted to be relevant to the medical condition.

In some implementations, determining, for each brain parcel of multiple brain parcels that are predicted to be relevant to the medical condition, a respective brain network affiliation includes: determining a number of brain parcels of multiple brain parcels that are predicted to be relevant to the medical condition that are associated with a particular brain network of multiple brain networks.

In some implementations, the visualization is a divided bar chart that visually indicates, for each brain network of multiple brain networks, the number of brain parcels that are predicted to be relevant to the medical condition.

In some implementations, multiple brain parcels that are predicted to be relevant to the medical condition have been identified by operations including: training a machine learning model to process an input derived from brain data for a brain of an input patient to predict whether the input patient has the medical condition, and identifying multiple brain parcels that are predicted to be relevant to the medical condition using the machine learning model.

In some implementations, identifying multiple brain parcels that are predicted to be relevant to the medical condition using the machine learning model includes: determining, for each brain parcel in a parcel atlas, a respective importance score for the brain parcel that measures an impact of the brain parcel on predictions generated by the machine learning model, and identifying multiple brain parcels that are predicted to be relevant to the medical condition using the importance scores for the brain parcels in the parcel atlas.

In some implementations, identifying multiple brain parcels that are predicted to be relevant to the medical condition using the importance scores for the brain parcels in the parcel atlas includes: identifying each brain parcel in the parcel atlas having an importance score that satisfies a predefined threshold as being relevant to the medical condition.

In some implementations, identifying multiple brain parcels that are predicted to be relevant to the medical condition using the importance scores for the brain parcels in the parcel atlas includes: identifying a predefined number of brain parcels that are associated with the highest importance scores from the brain parcels in the parcel atlas as being relevant to the medical condition.

According to a second aspect, there is provided a method that includes: receiving a selection of a medical condition, obtaining data identifying multiple brain parcels of a brain of a patient that are predicted to be relevant to the medical condition, determining, for each of multiple brain parcels that are predicted to be relevant to the medical condition, a respective brain network affiliation of the brain of the patient, generating, on a user device of a user, a visualization that includes one or more respective brain network affiliations determined for each of multiple brain parcels that are predicted to be relevant to the medical condition, and taking an action based on the visualization.

According to a third aspect, there is provided a system including: one or more computers, and one or more storage devices communicatively coupled to the one or more computers, where the one or more storage devices store instructions that, when executed by the one or more computers, cause the one or more computers to perform the operations of the method of any preceding aspect.

According to a fourth aspect, there are provided one or more non-transitory computer storage media storing instructions that when executed by one or more computers cause the one or more computers to perform the operations of the method of any preceding aspect.

Particular embodiments of the subject matter described in this specification can be implemented so as to realize one or more of the following advantages.

Typically, outcome data from machine learning models relating to various symptom profiles can be highly complex and difficult to interpret at scale. In some cases, outcome data for the patient can include as many as twenty or more different symptoms and medical conditions, in a variety of different combinations. Brain data typically has high dimensionality and involves mixed type variables with complex, non-linear relationships. Accordingly, there exists a growing need for methods and systems that can not only generate prediction outcomes, but also interpret them particularly in the context of complex relationships surrounding various brain disease states.

The methods described in this specification can use brain data for the brain of a patient and the predicted outcome of the machine learning model to generate a visualization that explains the relationship between various features (e.g., brain parcels and brain networks) towards the predicted outcome. In particular, methods described in this specification enable interpretability of the predicted outcome using different hierarchical levels of structural and functional aspects of the brain of the patient, e.g., the methods can provide the basis of a predicted outcome using individual brain networks, individual brain parcels, and the relationship between brain parcels and their respective brain network affiliations. Accordingly, the method described in this specification can interpret high-dimensional and complex machine learning predictions and related connectome interactions in the context of human neuroimaging datasets investigating brain pathology, in an easy-to-understand way. Therefore, the method can assist clinicians in determining appropriate diagnoses, treatments, or surgical procedures to treat the medical condition in the patient.

The details of one or more embodiments of the patient matter of this specification are set forth in the accompanying drawings and the description below. Other features, aspects, and advantages of the patient matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1A:
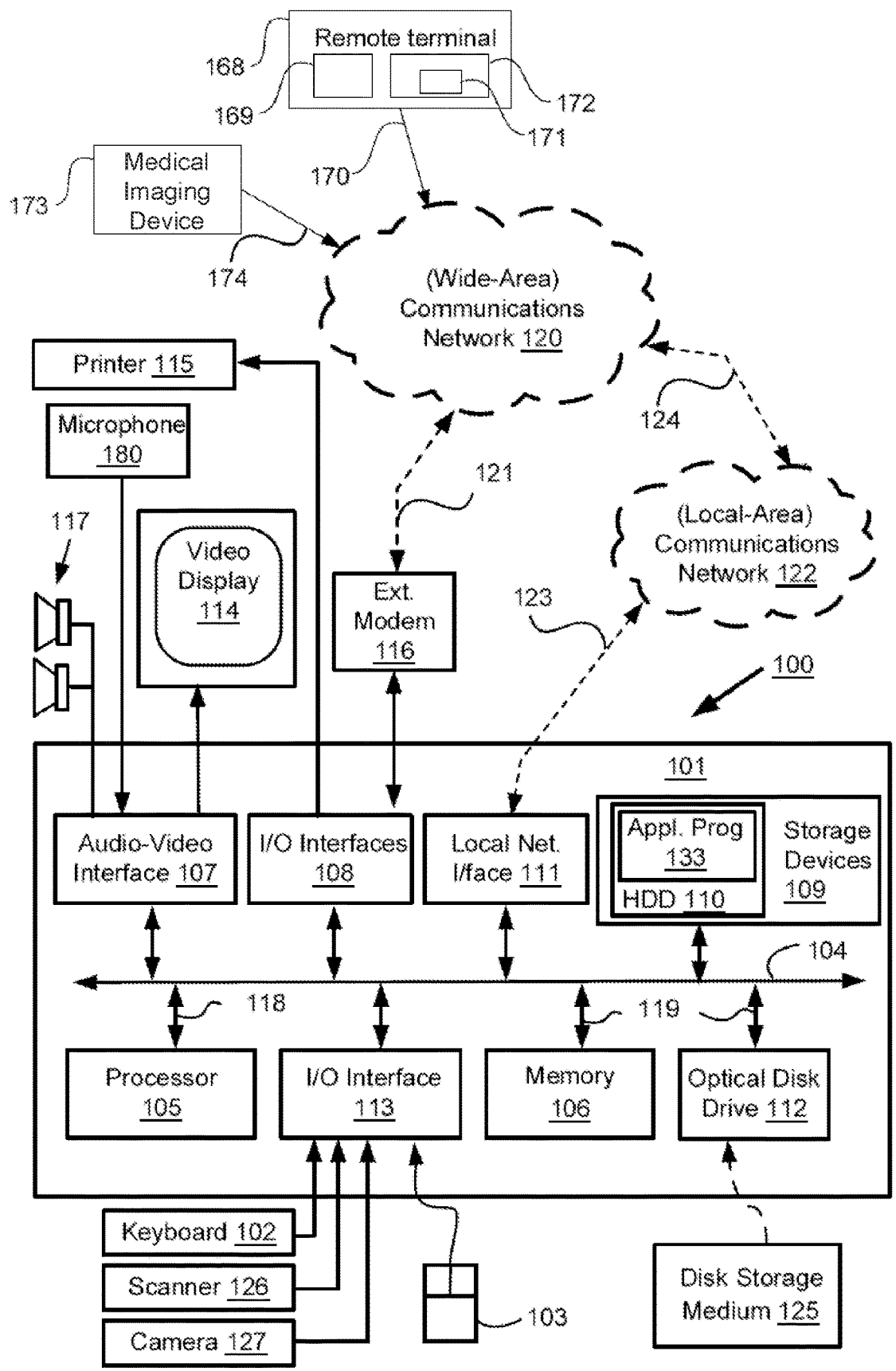
FIG. 1A and FIG. 1B are block diagrams that illustrate an example computer system for use in processing medical images.

This specification described a method for using brain data for a brain of a patient, and a predicted outcome related to a medical condition, e.g., obtained by using a machine learning model, to generate a visualization of complex connectome interactions that contribute to the predicted outcome for the patient.

The "brain data" can refer to data that characterizes connectivity in the brain of the patient and, in some cases, brain activity patterns in the brain of the patient. Brain data can be obtained by processing an image of the brain obtained using any suitable medical imaging technique including, e.g., Magnetic Resonance Imaging (MRI), functional Magnetic Resonance Imaging (fMRI), functional Near-Infrared Spectroscopy (fNIRS), Magnetoencephalography (MEG), Electroencephalography (EEG), Diffusion Tensor Imaging (DTI), or any other appropriate imaging technique.

The method described in this specification can process brain data of the brain of the patient using a machine learning model to generate a prediction that characterizes a likelihood that the patient has the medical condition. In some implementations, the prediction can relate to, e.g., a symptom, a behavior, or a trait. As a particular example, the medical condition can be, e.g., depression, anxiety, or schizophrenia. In some cases, the prediction generated by the machine learning model can be a binary classification, e.g., predicting the presence or absence of the medical condition.

The method described in this specification can use brain data and a predicted outcome of a machine learning model to generate a visualization of different brain networks contributing to the predicted outcome. Throughout this specification, a "brain network" can refer to a volume, or region, of the brain that has particular structural characteristics and is associated with one or more functions in the brain. Generally, the brain of the patient can be categorized to include multiple brain networks, e.g., between six and thirty major brain networks. In some cases, each of the brain networks can exhibit community structure, e.g., the brain network can include neurons, or nerve tracts, that are densely connected within the selected brain network, and are sparsely connected with the neurons, or nerve tracts, included in the other non-selected brain networks.

The brain can be partitioned into multiple brain networks using any of a variety of techniques. In one example, in order to determine a partition of the brain into different brain networks, brain data can be processed using, e.g., clustering algorithms (e.g., hierarchical clustering) or community detection algorithms. Example brain networks can include: the default mode network, the cortical visual network, the somatomotor network, the central executive network, the ventral salience network, and the dorsal salience network.

Throughout this specification, a "brain parcel" can refer to a region, e.g., a three-dimensional (3-D) volumetric region, of the brain. Typically, a parcel refers to a region that has a specified function, structural connectivity, or cellular composition. A collection of parcels that collectively define a partition of the brain may be referred to as a "parcel atlas." A parcel atlas can include a plurality of parcels, e.g., between 50 and 1000 parcels such as 50 parcels, 100 parcels, 389 parcels, 500 parcels, or 1000 parcels.

Generally, a parcel atlas can be chosen such that each parcel in the parcel atlas is expected to have broadly similar properties (e.g., functional activity, structural connectivity, or cellular composition) between patients, even if the exact boundaries of the parcel differ between patients. A parcel atlas can be a useful mechanism for analyzing brain images as it reduces the complexity of the brain architecture to a finite number of domains, which can be expected to play somewhat uniform roles in normal operation of the brain.

In some cases, each brain parcel can represent a sub-region of the brain that expresses similar properties in a population, even if the exact boundaries or topological location of the brain parcel in the brain differs between individuals. Some brain parcels can be included in, or affiliated with, more than one brain network, e.g., some brain parcels can overlap multiple brain networks.

The method described in this specification can identify a set of (multiple) "high-impact" (or "high contribution" or "high protection") brain parcels, from the parcel atlas, that are predicted to be relevant to the medical condition, e.g., if neural activity in the brain parcel is associated with the cause or mechanism of the medical condition in at least some patients. For example, a high-impact parcel can be part of a malfunctioning neural circuit that contributes to the medical condition in a target patient. For each of high-impact brain parcels, the method can automatically identify the respective brain network affiliation in the brain of the patient. The method can generate a visualization that demonstrates, and graphically organizes, complex connectome interactions of brain parcels, and their respective brain network affiliations, in the context of a particular medical condition.

Example systems that can perform the aforementioned method will be described in more detail next.

Figure 1B:
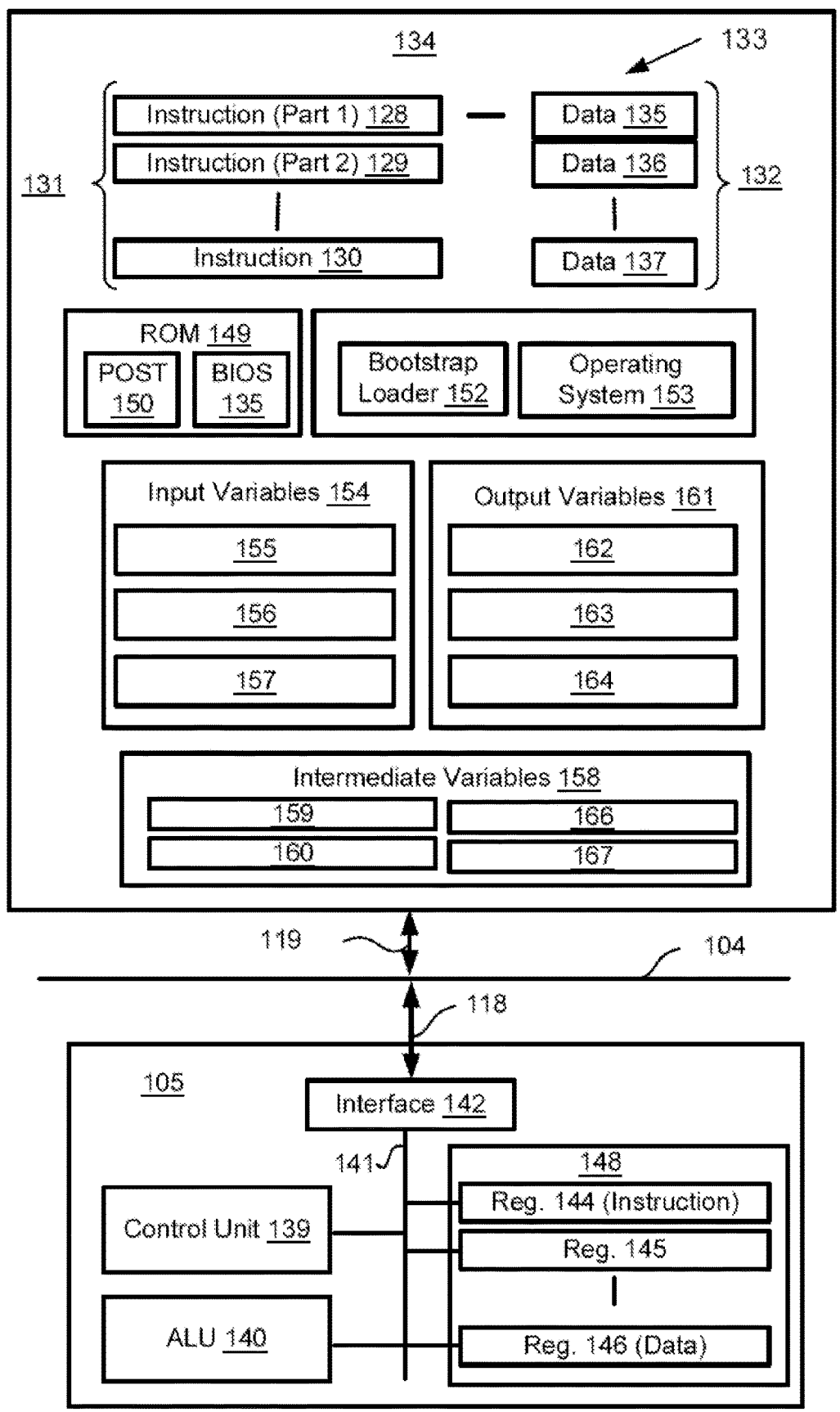

FIGS. 1A and 1B are block diagrams of a computer system 100 upon which one can practice arrangements described in this specification. The following description is directed primarily to a computer server module 101. However, the description applies equally or equivalently to one or more remote terminals 168.

As seen in FIG. 1A, the computer system 100 includes: the server computer module 101; input devices such as a keyboard 102, a pointer device 103 (e.g., a mouse), a scanner 126, a camera 127, and a microphone 180; and output devices including a printer 115, a display device 114 and loudspeakers 117. An external Modulator-Demodulator (Modem) transceiver device 116 may be used by the computer server module 101 for communicating to and from the remote terminal 168 over a computer communications network 120 via a connection 121 and a connection 170. The aforementioned communication can take place between the remote terminal 168 and "the cloud" which in the present description comprises at least the one server module 101. The remote terminal 168 typically has input and output devices (not shown) which are similar to those described in regard to the server module 101. The communications network 120 may be a wide-area network (WAN), such as the Internet, a cellular telecommunications network, or a private WAN. Where the connection 121 is a telephone line, the modem 116 may be a traditional "dial-up" modem. Alternatively, where the connection 121 is a high capacity (e.g., cable) connection, the modem 116 may be a broadband modem. A wireless modem may also be used for wireless connection to the communications network 120.

The computer server module 101 typically includes at least one processor unit 105, and a memory unit 106. For example, the memory unit 106 may have semiconductor random access memory (RAM) and semiconductor read only memory (ROM). The remote terminal 168 typically includes at least one processor 169 and a memory 172. The computer server module 101 also includes a number of input/output (I/O) interfaces including: an audio-video interface 107 that couples to the video display 114, loudspeakers 117 and microphone 180; an I/O interface 113 that couples to the keyboard 102, mouse 103, scanner 126, camera 127 and optionally a joystick or other human interface device (not illustrated); and an interface 108 for the external modem 116 and printer 115. In some implementations, the modem 116 may be incorporated within the computer module 101, for example within the interface 108. The computer module 101 also has a local network interface 111, which permits coupling of the computer system 100 via a connection 123 to a local-area communications network 122, known as a Local Area Network (LAN). As illustrated in FIG. 1A, the local communications network 122 may also couple to the wide network 120 via a connection 124, which would typically include a so-called "firewall" device or device of similar functionality. The local network interface 111 may include an Ethernet circuit card, a Bluetooth® wireless arrangement or an IEEE 802.11 wireless arrangement; however, numerous other types of interfaces may be practiced for the interface 111.

The I/O interfaces 108 and 113 may afford either or both of serial or parallel connectivity; the former may be implemented according to the Universal Serial Bus (USB) standards and having corresponding USB connectors (not illustrated). Storage memory devices 109 are provided and typically include a hard disk drive (HDD) 110. Other storage devices such as a floppy disk drive and a magnetic tape drive (not illustrated) may also be used. An optical disk drive 112 is typically provided to act as a non-volatile source of data. Portable memory devices, optical disks (e.g., CD-ROM, DVD, Blu-ray Disc™), USB-RAM, portable, external hard drives, and floppy disks, for example, may be used as appropriate sources of data to the system 100.

The components 105 to 113 of the computer module 101 typically communicate via an interconnected bus 104 and in a manner that results in a conventional mode of operation of the computer system 100 known to those in the relevant art. For example, the processor 105 is coupled to the system bus 104 using a connection 118. Likewise, the memory 106 and optical disk drive 112 are coupled to the system bus 104 by connections 119.

The techniques described in this specification may be implemented using the computer system 100, e.g., may be implemented as one or more software application programs 133 executable within the computer system 100. In some implementations, the one or more software application programs 133 execute on the computer server module 101 (the remote terminal 168 may also perform processing jointly with the computer server module 101), and a browser 171 executes on the processor 169 in the remote terminal, thereby enabling a user of the remote terminal 168 to access the software application programs 133 executing on the server 101 (which is often referred to as "the cloud") using the browser 171. In particular, the techniques described in this specification may be implemented by instructions 131 (see FIG. 1B) in the software 133 that are carried out within the computer system 100. The software instructions 131 may be formed as one or more code modules, each for performing one or more particular tasks. The software may also be divided into two separate parts, in which a first part and the corresponding code modules perform the described techniques and a second part and the corresponding code modules manage a user interface between the first part and the user.

The software may be stored in a computer readable medium, including the storage devices described below. The software is loaded into the computer system 100 from the computer readable medium, and then executed by the computer system 100. A computer readable medium having such software or computer program recorded on the computer readable medium is a computer program product. Software modules that execute techniques described in this specification may also be distributed using a Web browser.

The software 133 is typically stored in the HDD 110 or the memory 106 (and possibly at least to some extent in the memory 172 of the remote terminal 168). The software is loaded into the computer system 100 from a computer readable medium, and executed by the computer system 100. Thus, for example, the software 133, which can include one or more programs, may be stored on an optically readable disk storage medium (e.g., CD-ROM) 125 that is read by the optical disk drive 112. A computer readable medium having such software or computer program recorded on it is a computer program product.

In some instances, the application programs 133 may be supplied to the user encoded on one or more CD-ROMs 125 and read via the corresponding drive 112, or alternatively may be read by the user from the networks 120 or 122. Still further, the software can also be loaded into the computer system 100 from other computer readable media. Computer readable storage media refers to any non-transitory tangible storage medium that provides recorded instructions and/or data to the computer system 100 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a PCMCIA card and the like, whether or not such devices are internal or external of the computer module 101. Examples of transitory or non-tangible computer readable transmission media that may also participate in the provision of software, application programs, instructions and/or data to the computer module 101 include radio or infrared transmission channels as well as a network connection to another computer or networked device, and the Internet or Intranets including e-mail transmissions and information recorded on Websites and the like.

The second part of the application programs 133 and the corresponding code modules mentioned above may be executed to implement one or more graphical user interfaces (GUIs) to be rendered or otherwise represented upon the display 114. For example, through manipulation of the keyboard 102 and the mouse 103, a user of the computer system 100 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 117 and user voice commands input via the microphone 180.

FIG. 1B is a detailed schematic block diagram of the processor 105 and a "memory" 134. The memory 134 represents a logical aggregation of all the memory modules (including the HDD 109 and semiconductor memory 106) that can be accessed by the computer module 101 in FIG. 1A.

When the computer module 101 is initially powered up, a power-on self-test (POST) program 150 can execute. The POST program 150 can be stored in a ROM 149 of the semiconductor memory 106 of FIG. 1A. A hardware device such as the ROM 149 storing software is sometimes referred to as firmware. The POST program 150 examines hardware within the computer module 101 to ensure proper functioning and typically checks the processor 105, the memory 134 (109, 106), and a basic input-output systems software (BIOS) module 151, also typically stored in the ROM 149, for correct operation. Once the POST program 150 has run successfully, the BIOS 151 can activate the hard disk drive 110 of FIG. 1A. Activation of the hard disk drive 110 causes a bootstrap loader program 152 that is resident on the hard disk drive 110 to execute via the processor 105. This loads an operating system 153 into the RAM memory 106, upon which the operating system 153 commences operation. The operating system 153 is a system level application, executable by the processor 105, to fulfill various high-level functions, including processor management, memory management, device management, storage management, software application interface, and generic user interface.

The operating system 153 manages the memory 134 (109, 106) to ensure that each process or application running on the computer module 101 has sufficient memory in which to execute without colliding with memory allocated to another process. Furthermore, the different types of memory available in the system 100 of FIG. 1A must be used properly so that each process can run effectively. Accordingly, the aggregated memory 134 is not intended to illustrate how particular segments of memory are allocated (unless otherwise stated), but rather to provide a general view of the memory accessible by the computer system 100 and how such is used.

As shown in FIG. 1B, the processor 105 includes a number of functional modules including a control unit 139, an arithmetic logic unit (ALU) 140, and a local or internal memory 148, sometimes called a cache memory. The cache memory 148 typically includes a number of storage registers 144-146 in a register section. One or more internal busses 141 functionally interconnect these functional modules. The processor 105 typically also has one or more interfaces 142 for communicating with external devices via the system bus 104, using a connection 118. The memory 134 is coupled to the bus 104 using a connection 119.

The application program 133 includes a sequence of instructions 131 that may include conditional branch and loop instructions. The program 133 may also include data 132 which is used in execution of the program 133. The instructions 131 and the data 132 are stored in memory locations 128, 129, 130 and 135, 136, 137, respectively. Depending upon the relative size of the instructions 131 and the memory locations 128-130, a particular instruction may be stored in a single memory location as depicted by the instruction shown in the memory location 130. Alternatively, an instruction may be segmented into a number of parts each of which is stored in a separate memory location, as depicted by the instruction segments shown in the memory locations 128 and 129.

In general, the processor 105 is given a set of instructions which are executed therein. The processor 105 waits for a subsequent input, to which the processor 105 reacts to by executing another set of instructions. Each input may be provided from one or more of a number of sources, including data generated by one or more of the input devices 102, 103, data received from an external source 173, e.g., a medical imaging device 173 such as an MM or DTI scanner, X-ray, ultrasound or other medical imaging device across one of the networks 120, 122, data retrieved from one of the storage devices 106, 109 or data retrieved from a storage medium 125 inserted into the corresponding reader 112, all depicted in FIG. 1A. The execution of a set of the instructions may in some cases result in output of data. Execution may also involve storing data or variables to the memory 134.

Some techniques described in this specification use input variables 154, e.g., data sets characterizing one or more anatomical or surgical structures, which are stored in the memory 134 in corresponding memory locations 155, 156, 157. The techniques can produce output variables 161, which are stored in the memory 134 in corresponding memory locations 162, 163, 164. Intermediate variables 158 may be stored in memory locations 159, 160, 166 and 167.

Referring to the processor 105 of FIG. 1B, the registers 144, 145, 146, the arithmetic logic unit (ALU) 140, and the control unit 139 work together to perform sequences of micro-operations needed to perform "fetch, decode, and execute" cycles for every instruction in the instruction set making up the program 133. Each fetch, decode, and execute cycle can include i) a fetch operation, which fetches or reads an instruction 131 from a memory location 128, 129, 130; ii) a decode operation in which the control unit 139 determines which instruction has been fetched; and iii) an execute operation in which the control unit 139 and/or the ALU 140 execute the instruction.

Thereafter, a further fetch, decode, and execute cycle for the next instruction may be executed. Similarly, a store cycle may be performed by which the control unit 139 stores or writes a value to a memory location 132.

Each step or sub-process in the techniques described in this specification may be associated with one or more segments of the program 133 and is performed by the register section 144, 145, 146, the ALU 140, and the control unit 139 in the processor 105 working together to perform the fetch, decode, and execute cycles for every instruction in the instruction set for the noted segments of the program 133. Although a cloud-based platform has been described for practicing the techniques described in this specification, other platform configurations can also be used. Furthermore, other hardware/software configurations and distributions can also be used for practicing the techniques described in this specification.

Figure 2:
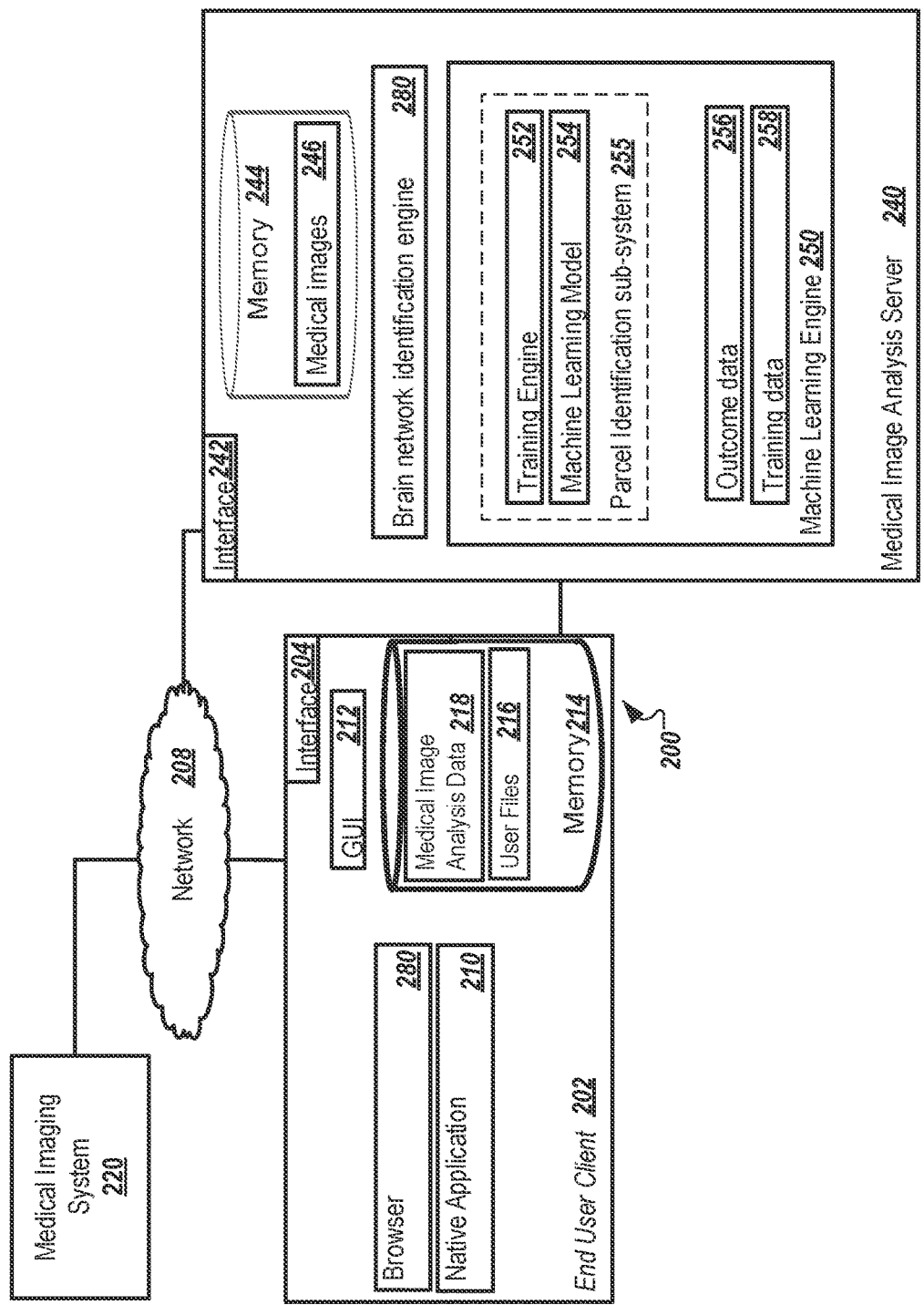
FIG. 2 is a block diagram of an example system for visualizing complex connectome interactions relevant to a medical condition.

FIG. 2 is a block diagram illustrating an example system 200 for visualizing complex connectome interactions relevant to a medical condition, a symptom, a behavior, or a trait. The system of FIG. 2 may be implemented within a computer system as described with reference to FIGS. 1A and 1B. Specifically, the illustrated system 200 includes or is communicably coupled with a Medical Image Analysis server 240, an end-user client device 202, a network 208 (which can include a local area network (LAN), a wide area network (WAN), the Internet, or a combination thereof), and a medical imaging system 220. Although shown separately, in some implementations, functionality of two or more systems, devices, or servers may be provided by a single system or server. In some implementations, the functionality of one illustrated system, server, or engine may be provided by multiple systems, servers, or engines, respectively.

An end-user client device 202 (also referred to herein as client device 202 or device 202) is an electronic device that is capable of requesting and receiving content over the network 208. The end-user client device 202 can include any client computing device such as a laptop/notebook computer, wireless data port, smart phone, personal data assistant (PDA), tablet computing device, one or more processors within these devices, or any other suitable processing device that can send and receive data over the network 208. For example, the end-user client device 202 can include, e.g., a computer that includes an input device, such as a keypad, touch screen, or other device that can accept user information, and an output device that conveys information, e.g., associated with the operation of the Medical Image Analysis server 240, or the client device itself, including digital data, visual information, or the GUI 212. The end-user client device 202 can include one or more client applications (as described above). A client application is any type of application that allows the end-user client device 202 to request and view content on a respective client device. In some implementations, a client application can use parameters, metadata, and other information received, e.g., at launch, to access a particular set of data from the Medical Image Analysis server 240. In some instances, a client application may be an agent or client-side version of the one or more enterprise applications running on an enterprise server (not shown).

Figure 6:
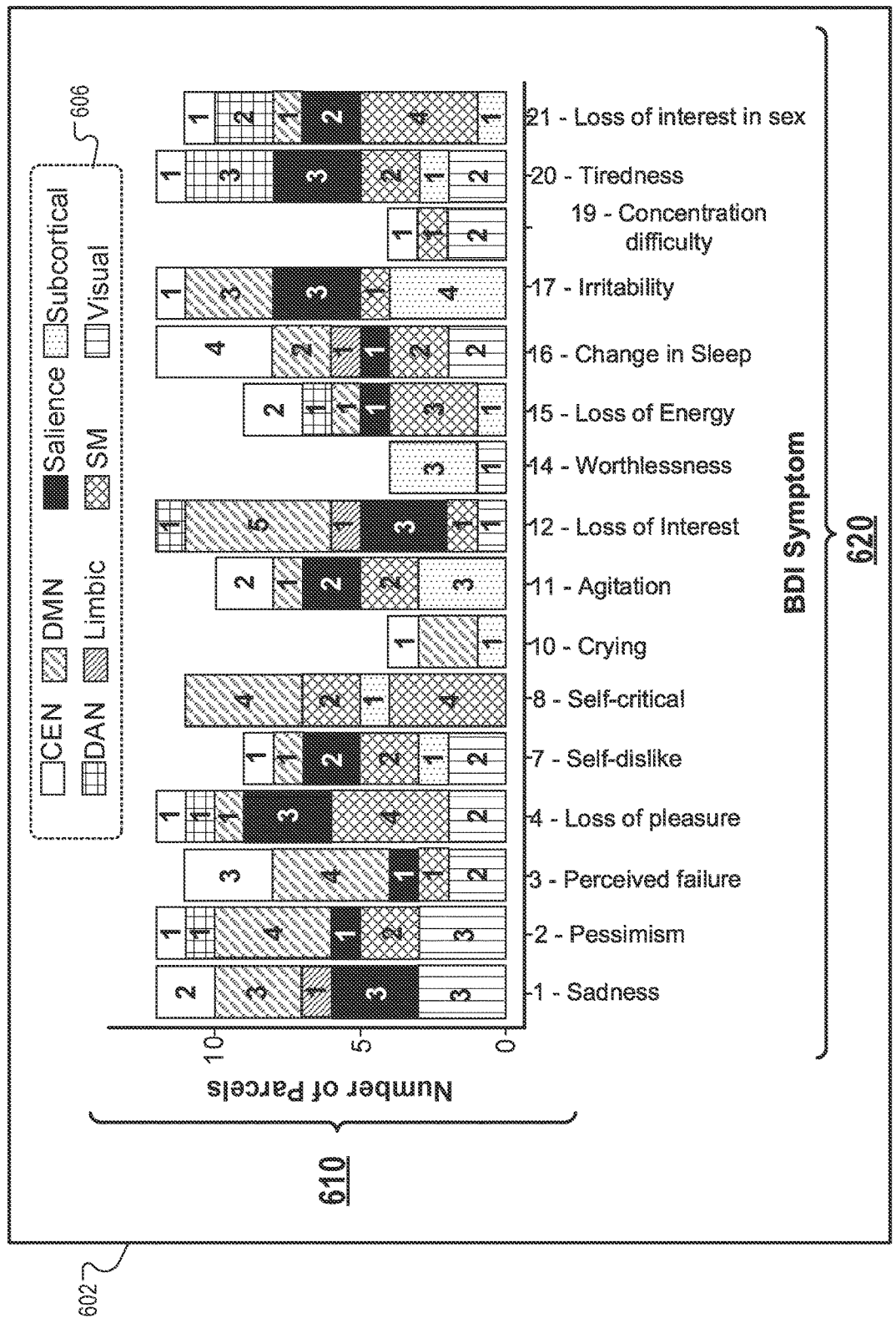
FIG. 6 illustrates an example graphical user interface displaying a visualization of complex connectome interactions relevant to a medical condition.

The end-user client device 202 typically includes one or more applications, such as a browser 280 or a native application 210, to facilitate sending and receiving of content over the network 108. Examples of content presented at a client device 202 include images from medical imaging system 220, and a visualization of complex connectome interactions relevant to a medical condition, e.g., as shown in FIG. 6.

Medical imaging system 220 can be any appropriate imaging system, for example an Mill system, CT system, X-ray system, EEG system or NIRS system. In an implementation, the medical imaging system may be a functional MRI (fMRI) imaging system to produce resting state fMRI images of the brain. In other examples the imaging data may selected from at least one of, Magnetoencephalograph (MEG), electroencephalograph (EEG), magnetic resonance imaging (MRI), and diffusion tensor imaging (DTI). While only one medical imaging system 220 is shown in FIG. 2, images can be received from multiple medical imaging systems.

An end user of the end-user client device 202 can provide an input to the Medical Image Analysis server 240 through a graphical user interface (GUI) 212. For example, the user can use a machine learning engine 250 included in the server 240 to carry out one or more tasks associated with analyzing one or more medical images. In one example, the tasks can include processing one or more images of the brain obtained by the medical imaging system 220 to generate brain data that characterizes structural, or functional, connectivity of the brain of the patient. In another example, the tasks can include processing the brain data to generate a prediction (e.g., an outcome data 256) that characterizes a likelihood that the patient has a particular medical condition, symptom, behavior, or trait. As a particular example, the task can include processing brain data for the brain of a patient and, based on the processed brain data, generating the prediction (e.g., the outcome data 256).

The user input can include, e.g., one or more selections of a series of medical images 246, such as fMRI images to make a measurement of functional and/or structural data. For example, systems described in this specification can process an fMRI image to derive a connectomic map of the brain of a patient suffering from, or displaying, a particular set of symptoms or behaviors. In another example, a series of images can be selected automatically by a machine learning engine 250. In another example, the user input can provide, e.g., one or multiple medical conditions, symptoms, behaviors or traits.

Once the end user provides the input, the machine learning engine 250 of the Medical Image Analysis server 240 can process the data associated with the user input to determine a likelihood that particular data derived from a brain activity sensing system, e.g., a connectivity matrix derived from the medical images 246, is associated with a particular behavior or symptom.

As described in more detail below with reference to FIG. 3, a parcel identification sub-system 255 can process, e.g., a selection of a medical condition (e.g., provided by a user through the end user client 202), and brain data of the brain of the patient, to identify a set of (multiple) high-impact brain parcels that are predicted to be relevant to the medical condition. The parcel identification sub-system 255 can identify high-impact brain parcels from a parcel atlas, e.g., a group of brain parcels that collectively define a partition of the brain into multiple brain regions. In some implementations, the brain parcels can be represented by a connectivity matrix that characterizes the strength of connections between different brain regions defined by respective brain parcels. In one example, there can be hundreds of brain parcels, e.g., 379 parcels, resulting in thousands of unique matrix elements, e.g., more than 1,000, more than 30,000 or more than 70,000 unique matrix elements.

The parcel atlas can include any appropriate number of parcels, e.g., 50 parcels, 100 parcels, 500 parcels, or 1000 parcels. As a particular example, the parcel identification sub-system 255 can designate fewer than 50%, fewer than 20%, fewer than 10%, fewer than 5%, or fewer than 1% of the parcels in the parcel atlas as being high-impact parcels for the medical condition. In other implementations, the parcel identification system can designate a fixed number (e.g., 5, 10 15, or 20) of high-impact parcels.

The parcel identification sub-system 255 can include a machine learning model 254 that can be used to generate the outcome data 256, and a training engine 252 that can train the machine learning model 254 to generate the outcome data 256, e.g., to identify one or more behaviors or symptoms associated with particular structures or variables in the series of medical images of the brain. The machine learning model 254 can be configured according to any appropriate machine learning algorithm, e.g., linear regression, logistic regression, Bayes classifiers, random classifiers, decision trees, and neural networks. As a particular example, the machine learning model 254 can be a boosted decision tree machine learning model.

In order to identify the high-impact parcels that are predicted to be relevant to the medical condition, the training engine 252 can train the machine learning model 254 to process an input derived from the brain data of the brain of the patient (e.g., one or more images of the brain, e.g., fMRI images) to predict whether the patient has the medical condition. In some implementations, the training engine 252 can train the machine learning model 254 using brain data of multiple different patients. After training, the machine learning model 254 can be used to generate the outcome data 256 for any patient.

As described in more detail below with reference to FIG. 3, after generating the outcome data 256, the machine learning model 254 can identify high-impact brain parcels by determining, for each brain parcel in the parcel atlas, a respective importance score that measures an impact of the brain parcel on the prediction generated by the machine learning model 254 (e.g., the outcome data 256). The machine learning model 254 can identify high-impact brain parcels for the medical condition based on these importance scores, e.g., by selecting brain parcels having importance scores that satisfy a particular threshold, or by selecting a number of brain parcels with the highest importance scores.

In some implementations, the outcome data 256 can be used to label the training data 258 used for training the machine learning model 254. For example, images of the brain of a patient who is suffering from, e.g., Alzheimer's disease, can be labeled through, e.g., manual annotation. These images can then be used by the training engine 252 to train the machine learning model 254.

The medical images analysis server 240 can further include a brain network identification engine 280. After selecting high-impact brain parcels, the parcel identification sub-system can provide data identifying these brain parcels to the brain network identification engine 280 that can process the data and identify a respective brain network affiliation for each of the high-impact brain parcels. Example brain network identification engine 280 is described in more detail below with reference to FIG. 4A, FIG. 4B, and FIG. 4C.

In some implementations, the end user of the client device 202 can store the received Medical Image Analysis data 218 in the client device 202's memory 214 (along with other user files 216 that may already be stored in the memory 214). Memory 214 included in the end-user client device 202 and memory 244, may each include any memory or database module and may take the form of volatile or non-volatile memory including, without limitation, magnetic media, optical media, random access memory (RAM), read-only memory (ROM), removable media, or any other suitable local or remote memory component.

Example parcel identification sub-system 255 is described in more detail next.

Figure 3:
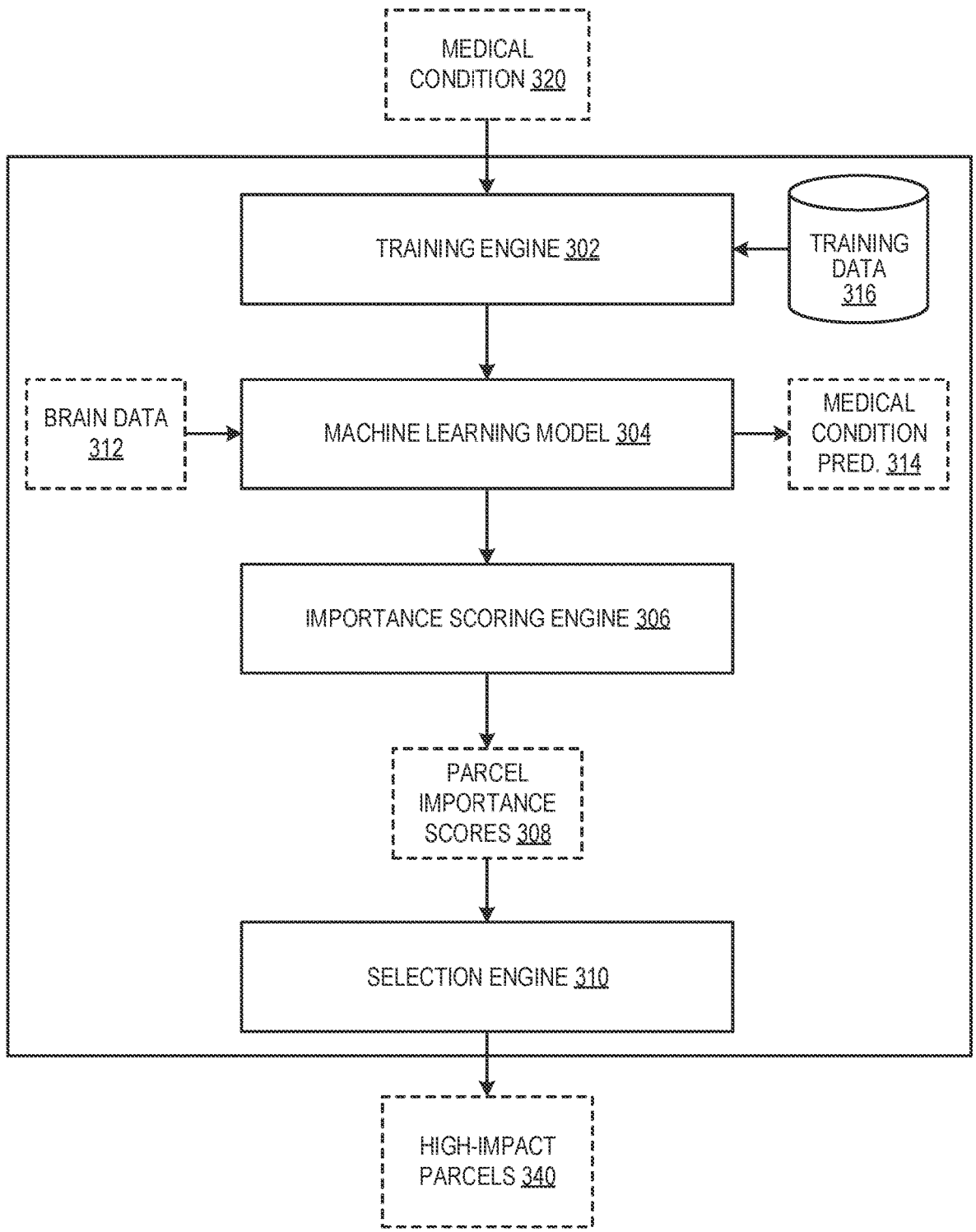
FIG. 3 is a block diagram of an example parcel identification sub-system of a system for visualizing complex connectome interactions relevant to a medical condition.

FIG. 3 is a block diagram of an example parcel identification sub-system 300. The parcel identification sub-system 300 can form a part of a system for visualizing complex connectome interactions relevant to a medical condition (e.g., the system 200 in FIG. 2). The parcel identification sub-system 300 is an example of a system implemented as computer programs on one or more computers in one or more locations in which the systems, components, and techniques described below are implemented.

The parcel identification sub-system 300 can be configured to receives brain data 312 for a brain of a patient, e.g., brain data characterizing the brain of the patient, or any other appropriate type of brain data, and process the brain data 312 to determine multiple brain parcels that contribute to a medical condition 320. For example, the sub-system 300 can, e.g., identify one or more parcels from a parcel atlas as being "high-impact" parcels 340, i.e., parcels that are predicted to be relevant to the medical condition 302, or parcels that have the most different activity (high or low) in patients with the condition relative to patients without the condition.

The parcel identification system 300 identifies the high-impact parcels using a training engine 302, a machine learning model 304, an importance scoring engine 306, and a selection engine 310, each of which described in more detail next.

The training engine 302 is configured to train the machine learning model 304 on a set of training data 316.

The machine learning model 304 is configured to process brain data 312 characterizing the brain of a patient to generate a prediction 314 for whether the patient has the medical condition 302.

The brain data 312 processed by the machine learning model 304 can be represented in a variety of possible ways, i.e., prior to being provided for processing by the machine learning model 304. For example, the brain data 312 can be represented as a "functional connectivity matrix" having a number of rows and columns equal to the number of parcels in the parcel atlas. The value at position (i, j) in the functional connectivity matrix can be defined as a correlation between the activity, e.g., the average blood flow curves, corresponding to parcel i and parcel j in the brain of the patient. As another example, the brain data 312 can be represented as a "functional connectivity vector" having a number of entries equal to the number of parcels in the parcel atlas. Each entry in the functional connectivity vector can be obtained by combining, e.g., summing or averaging, a corresponding row or column of the functional connectivity matrix.

The prediction 314 generated by the machine learning model 304 can define a predicted likelihood that the patient has the medical condition. In particular, the prediction 314 can be a numerical value, e.g., in the range [0,1], that defines a predicted likelihood of the patient having the medical condition.

The machine learning model 304 can be any model having a set of learnable parameters that can be trained to perform a prediction task. For example, the machine learning model 304 can include, e.g., a neural network model, a random forest model, a support vector machine model, a boosted decision tree, or a combination thereof.

The training data 316 includes multiple training examples, where each training example corresponds to a respective patient and includes: (i) brain data characterizing the brain of the patient, and (ii) a target output that identifies whether the patient has the medical condition 302. The training data 316 can include any appropriate number of training examples, e.g., 100 training examples, 1000 training examples, or 10,000 training examples. The training data 316 includes at least some training examples corresponding to patients that have the medical condition 302, and at least some training examples corresponding to patients that do not have the medical condition 302.

Generally, for each training example in the training data 316, the training engine 302 trains the machine learning model 304 to process the brain data included in the training example to generate a prediction that matches the target output specified by the training example.

The training engine 302 can train the machine learning model 304 on the training data 316 using any appropriate training technique. For example, if the machine learning model 304 is a neural network model, then the training engine 302 can train the machine learning model 304 using a stochastic gradient descent training technique.

The importance scoring engine 306 is configured to generate a respective importance score 308 for each parcel in the parcel atlas, where the importance score 308 for a parcel measures the impact of the parcel on predictions generated by the (trained) machine learning model 304. The impact of a parcel on predictions generated by the machine learning model 304 can refer to, e.g., a scale of the change in predictions generated by the machine learning model 304 that would result from modifying the portion of the brain data characterizing neural activity in the parcel.

The importance scoring engine 306 can generate the importance scores 308 for the parcels in the parcel atlas using any appropriate technique. In one example, the technique can be a "Hollow-tree Super" (HOTS) technique that can resolve and visualize importance scores 308 in, e.g., boosted tree machine learning models involving a relatively large number of features (e.g., parcels). An example implementation of the HOTS technique by the importance scoring engine 306 is described in more detail next.

The importance scoring engine 306 can obtain each brain parcel's contribution to each predicted outcome of the machine learning model by using, e.g., a Python package (e.g., eli5 explain_prediction) that is based on the LIME (Local Interpretable Model-agnostic Explanations) technique. For example, the importance scoring engine 306 can process the machine learning model and the predicted outcome to generate an output that specifies weights assigned to each brain parcel in the decision (e.g., the predicted outcome) made by the machine learning model. In some implementations, the weight of each brain parcel can be, e.g., the log odds contribution of each brain parcel to the predicted outcome (i.e. for positive class predictions, the weights are the log odds of being in the positive class). Example LIME technique that can be implemented by the importance scoring engine 306 is described in more detail with reference to: MT Ribeiro, et al., "Why should I trust you? Explaining the predictions of any classifier," Proceedings of the 22nd ACM SIGKDD international conference on knowledge discovery and data mining, 2016.

After generating the weights for each brain parcel, the importance scoring engine 306 can separate the weights contributing towards the positive and negative class cases, e.g., separate the weights according to a positive predictive likelihood of the patient having the medical condition, and a negative predictive likelihood of the patient having the medical condition, respectively.

In some implementations, the importance scoring engine 306 can perform the aforementioned steps for the predictions generated by the machine learning data for bran data of multiple different patients. In such cases, the importance scoring engine 306 can identify incorrect predictions (e.g., patients incorrectly identified as having the medical condition, or not having the medical condition), and predictions with a relative low probability, e.g., less than 70% confidence that the patient has the medical condition, and filter out such predictions. This assessment can be made based on, e.g., clinical data of each of the patients. Accordingly, the importance scoring engine 306 can keep only the patients that were correctly predicted, or classified, by the machine learning model as belonging to positive/negative class with confidence.

Next, the importance scoring engine 306 can obtain an average weight for each brain parcel per prediction generated by the machine learning model. For example, the importance scoring engine 306 can aggregate the weights across all the remaining predictions (e.g., those that have not been filtered out) by brain parcel, and divide by the total number of predictions, thereby obtaining the average weight of each feature per prediction.

In some implementations, the importance scoring engine 306 can infer not only the magnitude (e.g., the weight) of each brain parcel on the predicted outcome, but also a directionality of each brain parcel on the prediction made by the machine learning model (e.g., classification of the patient into a positive or negative class with regards to the medical condition). For example, as described above, the weight of each brain parcel is log odds of the class that is predicted by the machine learning model (i.e. for positive class predictions, the weights are the log odds of being in the positive class). Additionally, the weights are the log odds at the value of the feature currently being predicted. Accordingly, the importance scoring engine 306 can determine a sign (e.g., positive or negative) of the log odds for each brain parcel.

As a particular example, the importance scoring engine 306 can determine whether the mean value for each brain parcel in this positive class is greater or less than the mean of each corresponding brain parcel in the negative class.

Then, the importance scoring engine 306 can multiply the log odds (e.g., the weights) of each brain parcel in the positive class by the sign of the mean value for the positive class less the mean value for the negative class. On the other hand, the importance scoring engine 306 can multiply by the inverse sign of the same calculation the log odds of each brain parcel in the negative class. Therefore, the importance scoring engine 306 can generate weights that are log odds with appropriate directionality of each brain parcel on the prediction made by the machine learning model. These direction weights are the brain parcel importance scores 308.

In some implementations, the importance scoring engine 306 can also perform cross-validation across different brain datasets and brain parcels. This can allow for greater confidence when interpreting the prediction generated by the machine learning model 304 as it highlights only brain parcels that are consistent across runs. As a particular example, the importance scoring engine 306 can perform 5 fold cross-validation to obtain the mean parcel importance scores, with an average accuracy across all 5 folds, e.g., of 0.94.

Example techniques for generating the importance scores are described with reference to: S. Doyen et al., "Hollow-tree Super: a directional and scalable approach for feature importance in boosted tree models," arXiv:2104.03088 (2021); S. M. Lundberg et al., "A unified approach to interpreting model predictions," arXiv:1705.07874v2 (2017); M. T. Ribeiro et al., "Why should I trust you: explaining the prediction of any classifier," Proceedings of the 22nd ACM SIGKDD International Conference on Knowledge Discovery and Data Mining, pp. 1135-1144 (2016).

Although a particular example technique is described above, the importance scoring engine 306 can determine the parcel importance scores 308 in any other appropriate manner.

Generally, the importance score for a parcel can be understood as being proportionate to the relevance of the parcel to the medical condition. That is, a parcel associated with a higher importance score can be understood as being more relevant to the medical condition, e.g., because neural activity in that parcel has a higher impact on predictions, generated by the machine learning model.

The selection engine 310 is configured to receive the importance scores 308 for the parcels, and to designate a proper subset of the parcels in the parcel atlas as being high-impact parcels 304 based on the importance scores 308.

The selection engine 310 can select the high-impact parcels 304 from the parcel atlas based on the importance scores 308 of the parcels in the parcel atlas in any of a variety of ways. For example, the selection engine 310 can designate any parcel having an importance score 308 that satisfies (e.g., exceeds) a predefined threshold value as being a high-impact parcel 304. As another example, the selection engine 310 can designate a predefined number of parcels having the highest importance scores 308 as being high-impact parcels 304.

The parcel identification system 300 can determine high-impact parcels 304 for a variety of medical conditions using the techniques described above. The set of high-impact parcels for one medical condition will typically be different than the set of high-impact parcels for another medical condition, reflecting the diversity in underlying causes and mechanisms of medical conditions affecting the brain.

After determining the high-impact parcels 304 for the medical condition 302, the parcel identification sub-system 300 can provide data identifying the high-impact parcels 304 for the medical condition 302, e.g., to a brain network identification engine (e.g., the brain network identification engine 280 in FIG. 2). The brain network identification engine can process data identifying the high-impact parcels 304 to determine, for each high-impact parcel, a respective brain network affiliation.

The brain network identification engine is described in more detail below with reference to FIG. 4A, FIG. 4B, and FIG. 4C.

Figure 4A:
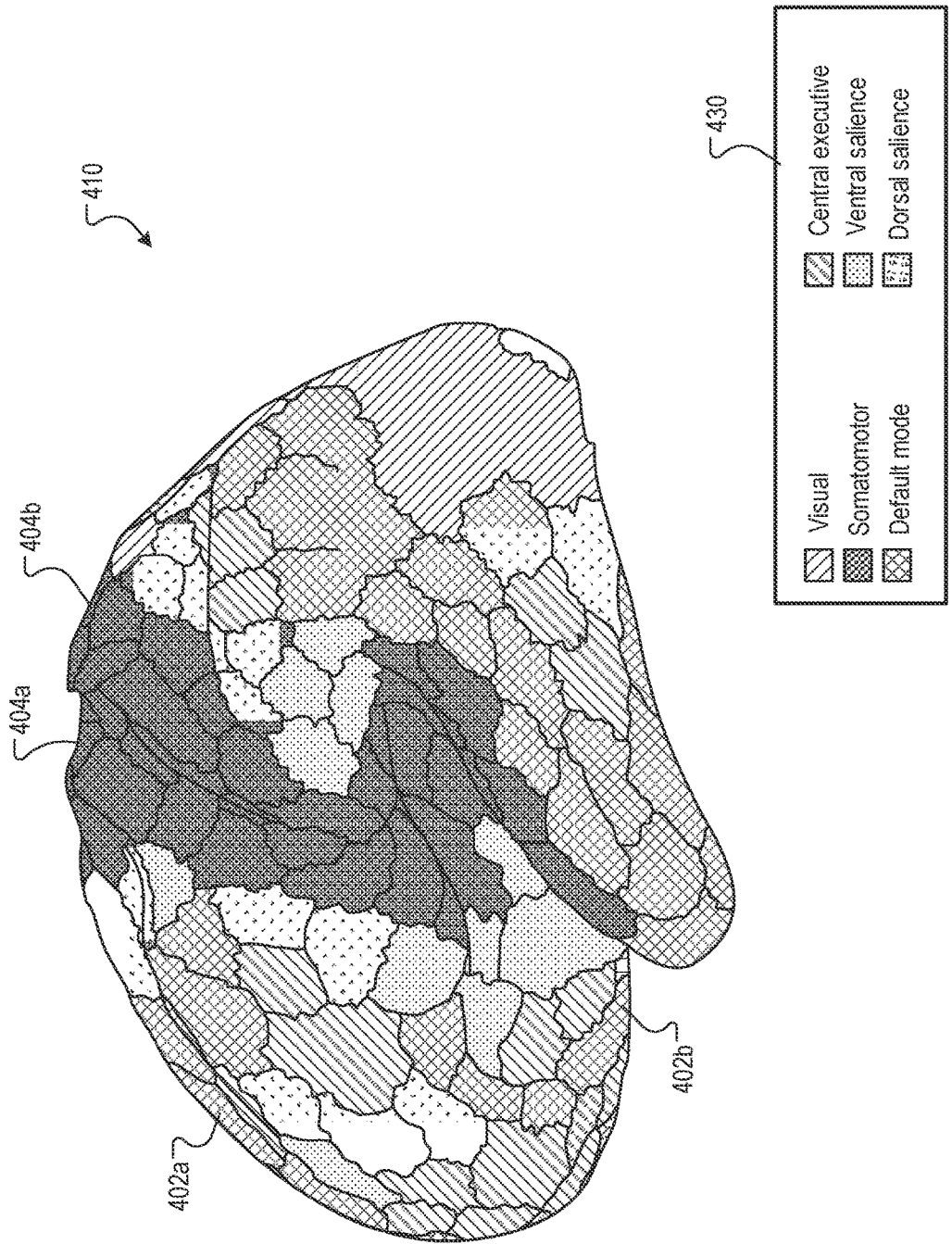
FIG. 4A illustrates example brain networks affiliations identified for each high-impact brain parcel by a brain network identification engine.
Figure 4C:
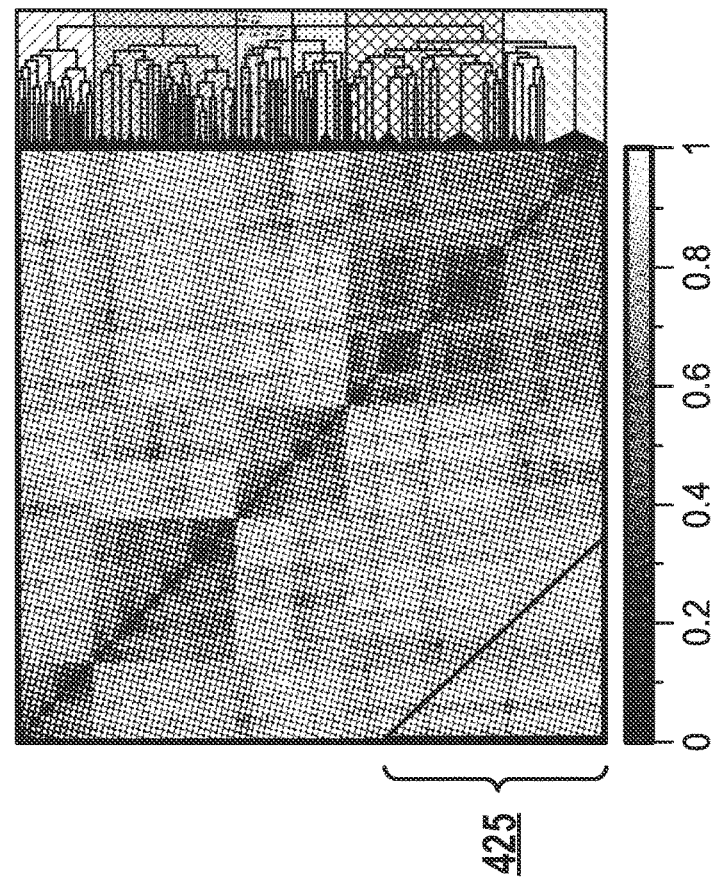
FIG. 4C illustrates a full view of a connectivity matrix generated for brain network affiliations.
Figure 4B:
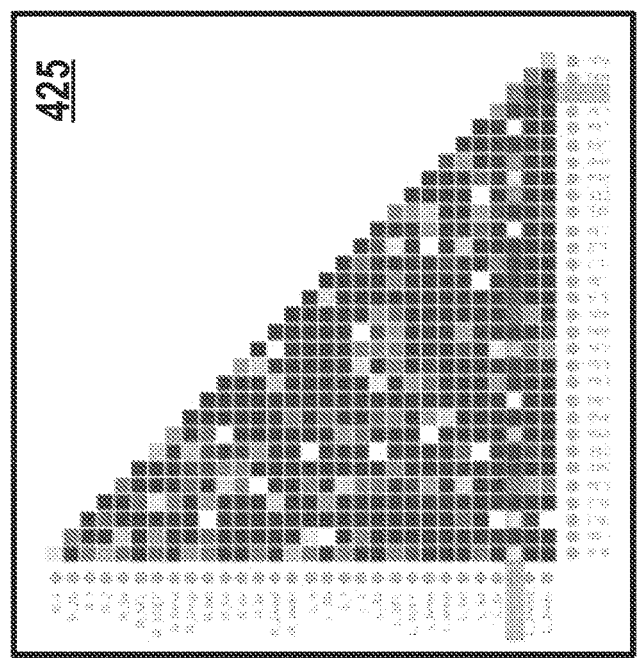
FIG. 4B illustrates a close-up view of a connectivity matrix generated for brain network affiliations.

FIG. 4A illustrates example brain network affiliations 400 identified for each high-impact brain parcel by a brain network identification engine. The brain network identification engine can be included in a system for visualizing complex connectome interactions relevant to a medical condition (e.g., the system 200 in FIG. 2) that is an example of a system implemented as computer programs on one or more computers in one or more locations in which the systems, components, and techniques described below are implemented.

As described above with reference to FIG. 3, a parcel identification sub-system (e.g., the sub-system 255 in FIG. 2) can be configured to receive brain data for a brain of a patient, e.g., brain data characterizing the brain of the patient, or any other appropriate type of brain data, and process the brain data to determine high-impact brain parcels that are predicted to be relevant to a medical condition. The brain network identification engine can process data identifying these high-impact brain parcels and determine a respective brain network affiliation for each of the brain parcels.

Generally, a "brain network" can refer to a volume, or region, of the brain that has particular structural characteristics and is associated with one or more functions in the brain. The brain can include multiple brain networks, e.g., between six and thirty major brain networks. In some cases, each of the brain networks can exhibit community structure, e.g., the brain network can include neurons, or nerve tracts, that are densely connected within the selected brain network, and are sparsely connected with the neurons, or nerve tracts, included in the other non-selected brain networks. Example brain networks can include a visual brain network, a somatomotor brain network, a default mode network, a central execute brain network, a ventral salience brain network, and a dorsal salience brain network.

The brain of the patient can be partitioned into multiple brain networks in any variety of ways. In one example, brain networks can be identified by processing brain data (e.g., fMRI images of the brain) using, e.g., a machine learning model configured according to clustering algorithms and/or community detection algorithms. As a particular example, brain networks can be identified using hierarchical clustering techniques. For example, the machine learning model can process brain data for the brain of the patient and generate a dendrogram 420 (e.g., characterizing a connectivity matrix as shown in FIGS. 4B and 4C) that represents a hierarchical organization of different communities in the brain resulting in six individual resting-state brain networks. In such cases, the brain networks represent, e.g., the smallest possible partition of the brain of the patient into multiple different communities, each community exhibiting community structure.

Example techniques for identifying brain networks in the brain are described in more detail with reference to: Akiki, T. J., Abdallah, C. G., "Determining the Hierarchical Architecture of the Human Brain Using Patient-Level Clustering of Functional Networks," Sci Rep 9, 19290 (2019) doi:

10.1038/s41598-019-55738-y. Although a particular example technique for identifying brain networks in the brain is described above, brain networks can also be identified in any other appropriate manner.

As described above, typically, a brain parcel can refer to a region of the brain that has a specified function, structural connectivity, or cellular composition. A collection of parcels that collectively define a partition of the brain can be referred to as a parcel atlas. Each brain parcel can be associated with a particular brain network. In one example, each brain network can include multiple brain parcels. In another example, some brain parcels can be included in more than one brain network, e.g., can overlap multiple brain networks.

The brain network identification engine can process data identifying the high-impact brain parcels that are predicted to be relevant to a medical condition and determine a respective brain network affiliation for each of these brain parcels based on, e.g., the parcel atlas and a codex that codifies which brain parcel in the parcel atlas belongs to which brain network. For example, the brain network identification engine can automatically map each brain parcel that is identified as being high-impact (e.g., by the parcel identification sub-system described above with reference to FIG. 3) onto the respective brain network. As a particular example, the brain network identification engine can generate a table that specifies, for each brain network (e.g., the default mode network), the number of brain parcels that are predicted to be relevant to the medical condition that are associated with this brain network.

For example, the parcel identification sub-system can identify a first brain parcel 404a, a second brain parcel 404b, a third brain parcel 402a, and a fourth brain parcel 402b as being most relevant to the symptom of anxiety. The sub-system can process data identifying these brain parcels and determine that the first brain parcel 404a and the second brain parcel 404b are associated with the somatomotor brain network, and that the third brain parcel 402a and the fourth brain parcel 402b are associated with the default mode network. Although only six brain networks 430 are illustrated in FIG. 4A, generally the brain network identification engine can identify high-impact parcels as belonging to a large number of brain networks. For example, as illustrated in the dendrogram 420 in FIG. 4C, each of the six brain networks 430 can be further subdivided into individual communities on a number of hierarchical levels, e.g., from six levels, corresponding to six individual relatively larger brain networks, to one hundred levels, corresponding to one hundred individual relatively smaller brain networks. The dendrogram 420 can include a connectivity matrix 425 that characterizes a connectivity in each of the brain networks, and sub-networks, e.g., as shown in the close-up view in FIG. 4B.

The brain network identification engine can provide data that specifies high-impact parcels for the medical condition, and their respective brain network affiliations, to a graphical user interface (e.g., the graphical user interface 212 in FIG. 2) that can generate a visualization that includes one or more respective brain network affiliations determined for each of the high-impact brain parcels that are predicted to be relevant to the medical condition. The visualization of connectome interactions can assist clinicians in determining appropriate diagnoses, treatments, or surgical procedures to treat the medical condition in the patient. Example visualization is described in more detail below with reference to FIG. 6.

Example process for generating a visualization of complex connectome interactions is described in more detail below with reference to FIG. 5.

Figure 5:
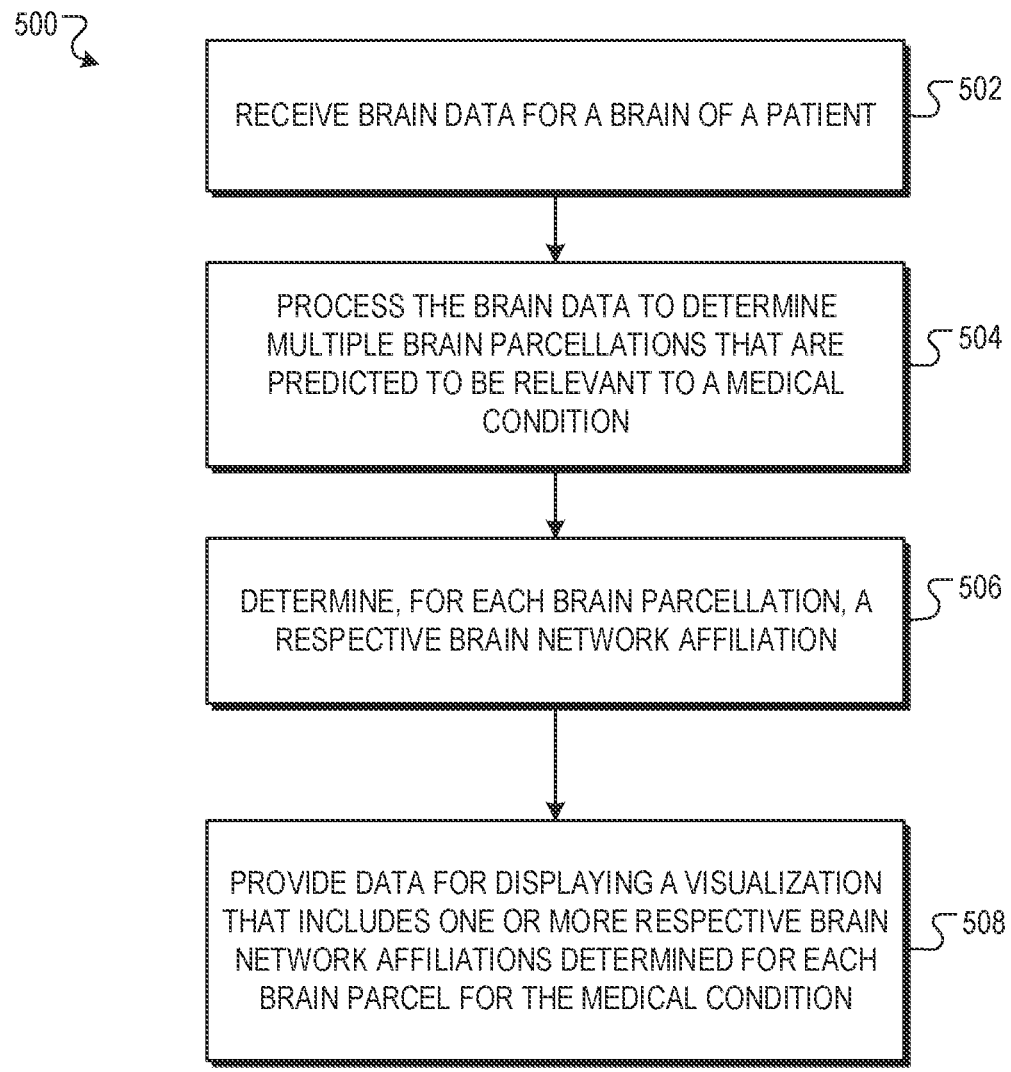
FIG. 5 is a flow diagram of an example process for visualizing complex connectome interactions relevant to a medical condition.

FIG. 5 is a flow diagram of an example process 500 for visualizing complex connectome interactions relevant to a medical condition. The process can be implemented by a combination of hardware, software, and firmware. For example, the systems described above with reference to FIGS. 1A, 1B, 2, 3, and 4, can be used to perform the process 500.

The system receives brain data for a brain of a patient (502). As described above with reference to FIG. 2, brain data can include one or more images of the brain of the patient (e.g., fMRI images of the brain), obtained using any appropriate brain imaging technique, or any other appropriate type of brain data. In some implementations, the system can receive brain data for the brain of multiple patients.

The system processes the brain data to determine multiple brain parcels that are predicted to be relevant to a medical condition (504). In some implementations, the system can receive a selection of the medical condition by a user through, e.g., a user client, as described above with reference to FIG. 2.

As described above with reference to FIG. 3, a brain parcel identification sub-system can process the brain data and determine one or more high-impact brain parcels that are predicted to be relevant to the medical condition. In cases where the system receive brain data for the brain of a cohort of patients, the system can identify brain parcels that are predicted to be relevant to the medical condition across the cohort of patients. As a particular example, the system can process the brain data for multiple patients using a machine learning model to generate outcome data, e.g., a prediction of which patients have the medical condition, and which do not have the medical condition. The system can filter out the patients that are predicted to not have the medical condition, and determine multiple brain parcels that are predicted to be relevant to the medical condition for the remaining patients.

In some implementations, the system can process brain data to determine multiple brain parcels that are predicted to be relevant to multiple medical conditions. For example, the system can process the brain data using the machine learning model to generate outcome data that specifies an individual prediction for each of multiple medical conditions. The system can filter out predictions that are negative (e.g., the patient not having the medical condition), and determine multiple brain parcels that are predicted to contribute to each of one or more remaining medical conditions.

The system determines, for each of multiple brain parcels that are predicted to be relevant to the medical condition, a respective brain network affiliation (506). As described above with reference to FIG. 4A, FIG. 4B, and FIG. 4C, a brain network identification engine can use, e.g., data identifying high-impact parcels received from the parcel identification sub-system, a brain parcel atlas and a codex to generate a table that specifies the number of high-impact brain parcels that are predicted to be relevant to the medical condition associated with one or more respective brain networks. In some implementations, such brain networks have been identified using a community detection algorithm, e.g., the brain networks can be resting-state brain networks that have been identified for the brain of a different patient, as specified in the codex.

The system provides, to a user device of a user, data for displaying a visualization that includes one or more respective brain network affiliations determined for each of multiple brain parcels that are predicted to be relevant to the medical condition (508). As described in more detail below with reference to FIG. 6, the visualization can be, e.g., a divided bar chart that specifies, for each of one or more medical conditions, the number of high-impact brain parcels that are predicted to be relevant to that medical condition.

In some implementations, the process 500 can further include taking an action based on the visualization. The action can be any appropriate action. In one example, the action can include exporting data identifying the one or more respective brain network affiliations for the medical condition.

Accordingly, the system can enable interpretability of the predicted outcome generated by the machine learning model on different hierarchical levels of structural and functional aspects of the brain of the patient, e.g., the system can interpret the outcome on the level of individual brain networks, individual brain parcels, and the relationship between brain parcels and their respective brain network affiliations. Furthermore, the system can generate a visualization that contextualizes the complex connectome interactions for an individual patient, or multiple patients, and for one or multiple medical conditions. Accordingly, the system can interpret high-dimensional and complex machine learning predictions and related connectome interactions in the context of human neuroimaging datasets, thereby assisting clinicians in understanding the relationships between different connectome interactions and designing effective treatment plans for specific brain pathologies.

Example visualization of complex connectome interactions is described in more detail next.

FIG. 6 illustrates an example graphical user interface 602 displaying a visualization of complex connectome interactions relevant to a medical condition. The graphical user interface 602 can be, e.g., the interface 212 described above with reference to FIG. 2 and can form a part of the system 200. A user (e.g., a clinician and/or a patient) can view the interface 602 in an end user client (e.g., the end user client 202 in FIG. 2) and interact with the client by, e.g., providing an input to the client. The visualization in FIG. 6 can be generated using the process 500 described above with reference to FIG. 5.

As described above, a machine learning model can process brain data to determine multiple brain parcels that contribute to a medical condition. The system can select a number of high-impact brain parcels, e.g., 20 top-contributing brain parcels, for the medical condition. For each of these brain parcels, the system described in this specification can determine a respective brain network affiliation.

The illustration in FIG. 6 shows the visualization that includes respective brain network affiliations determined for multiple medical conditions for a cohort of patients. However, the example of FIG. 6 is provided for illustrative purposes only, and the system described in this specification can generate a visualization for a single patient and a single medical condition, for a single patient and multiple medical conditions, or in any other appropriate manner.

In particular, FIG. 6 illustrates a divided bar chart that visually indicates the number of brain parcels that are affiliated with each of multiple respective brain networks. Specifically, the x-axis specifies a number of medical conditions 620, e.g., twenty one unique medical conditions, symptoms, behaviors or traits, e.g., "Sadness," "Pessimism," "Perceived failure," etc. The y-axis specifies the total number of brain parcels 610 (e.g., "Number of Parcels") that are top-contributing to the respective medical condition. For example, for the symptom of "Sadness," there are twelve top-contributing brain parcels. In another example, for the system of "Perceived failure," there are eleven top-contributing brain parcels. Generally, for each symptom, the visualization can indicate any number of brain parcels. In some implementations, the system can determine the number of top-contributing brain parcels based on a particular threshold of contribution values, e.g., the system can select the brain parcels having contribution values above a particular threshold.

As described above, for each of the top-contributing brain parcels, the system can identify respective brain network affiliations. Some brain parcels can be affiliated with more than one brain network. In FIG. 6, the visualization includes eight different brain networks 406, e.g., the default mode network "DMN," the visual network "Visual," etc. Although the visualization includes eight brain networks, the system can generate a visualization that includes any appropriate number of brain networks. In FIG. 6, each of the brain networks 606 is color coded. For example, the "Visual" brain network is cyan.

As described above, for each of the brain parcels that are relevant to the medical condition, the system identifies a respective brain network affiliation. In some cases, the system can group the top-contributing brain parcels according to their respective brain network affiliations. The number of brain parcels affiliated with each brain network are illustrated in the bar chart in FIG. 6. For example, as illustrated in FIG. 6, for the symptom "Sadness," three top-contributing brain parcels are affiliated with the "Visual" brain network, three top-contributing brain parcels are affiliated with the "Salience" brain network, one top-contributing brain parcel is affiliated with the "Limbic" brain network, three top-contributing brain parcels are affiliated with the "DMN" brain network, and two brain parcels are affiliated with the "CEN" brain network.

Accordingly, the visualization illustrated in FIG. 6 can allow the clinicians to break-down and interpret the predicted outcome (e.g., generated by the machine learning model) for a set of symptoms across a cohort of patients, or for a single patient, in the context of brain pathology. The machine learning models that generate the predicted outcomes can often provide complex outputs, and visualizing complex connectome interactions in an easy-to-digest way is critical in order to inform clinicians and facilitate effective decision making regarding the treatment of the patient.

Embodiments of the patient matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the patient matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the patient matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the patient matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the patient matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the patient matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method comprising:
receiving brain data for a brain of a patient;
processing the brain data to determine a plurality of brain parcels that are predicted to be relevant to a medical condition;
determining, for each of the plurality of brain parcels that are predicted to be relevant to the medical condition, a respective brain network affiliation; and
providing, to a user device of a user, data for displaying a visualization that includes one or more respective brain network affiliations determined for each of the plurality of brain parcels that are predicted to be relevant to the medical condition, wherein the plurality of brain parcels that are predicted to be relevant to the medical condition have been identified by operations comprising:
training a machine learning model to process an input derived from brain data for a brain of an input patient to predict whether the input patient has the medical condition; and
identifying the plurality of brain parcels that are predicted to be relevant to the medical condition using the machine learning model; and
wherein identifying the plurality of brain parcels that are predicted to be relevant to the medical condition using the machine learning model comprises:
determining, for each brain parcel in a parcel atlas, a respective importance score for the brain parcel that measures an impact of the brain parcel on predictions generated by the machine learning model; and
identifying the plurality of brain parcels that are predicted to be relevant to the medical condition using the importance scores for the brain parcels in the parcel atlas.

2. The method of claim 1, wherein the respective brain network affiliation specifies a brain network of a plurality of brain networks of the brain of the patient that have been identified using a hierarchical clustering algorithm.

3. The method of claim 1, wherein the respective brain network affiliation specifies a brain network of a plurality of brain networks of the brain of the patient and wherein the plurality of brain networks include one or more of: a visual brain network, a somatomotor brain network, a default mode network, a central execute brain network, a ventral salience brain network, and a dorsal salience brain network.

4. The method of claim 1, further comprising receiving brain data for a plurality of patients.

5. The method of claim 1, further comprising taking an action based on the visualization that includes one or more respective brain network affiliations determined for each of the plurality of brain parcels that are predicted to be relevant to the medical condition.

6. The method of claim 5, wherein taking the action based on the visualization that includes one or more respective brain network affiliations determined for each of the plurality of brain parcels that are predicted to be relevant to the medical condition comprises:
exporting data identifying the one or more respective brain network affiliations for the medical condition.

7. The method of claim 1, further comprising receiving a selection of the medical condition.

8. The method of claim 1, wherein the visualization further comprises a selection of the medical condition and an indication of the plurality of brain parcels that are predicted to be relevant to the medical condition.

9. The method of claim 1, wherein determining, for each brain parcel of the plurality of brain parcels that are predicted to be relevant to the medical condition, a respective brain network affiliation comprises:
determining a number of brain parcels of the plurality of brain parcels that are predicted to be relevant to the medical condition that are associated with a particular brain network of a plurality of brain networks.

10. The method of claim 9, wherein the visualization is a divided bar chart that visually indicates, for each brain network of the plurality of brain networks, the number of brain parcels that are predicted to be relevant to the medical condition.

11. The method of claim 1, wherein identifying the plurality of brain parcels that are predicted to be relevant to the medical condition using the importance scores for the brain parcels in the parcel atlas comprises:
identifying each brain parcel in the parcel atlas having an importance score that satisfies a predefined threshold as being relevant to the medical condition.

12. The method of claim 1, wherein identifying the plurality of brain parcels that are predicted to be relevant to the medical condition using the importance scores for the brain parcels in the parcel atlas comprises:
identifying a predefined number of brain parcels that are associated with the highest importance scores from the brain parcels in the parcel atlas as being relevant to the medical condition.

13. A system comprising:
one or more computers; and
one or more storage devices communicatively coupled to the one or more computers, wherein the one or more storage devices store instructions that, when executed by the one or more computers, cause the one or more computers to perform operations comprising:
receiving brain data for a brain of a patient;
processing the brain data to determine a plurality of brain parcels that are predicted to be relevant to a medical condition;
determining, for each of the plurality of brain parcels that are predicted to be relevant to the medical condition, a respective brain network affiliation; and
providing, to a user device of a user, data for displaying a visualization that includes one or more respective brain network affiliations determined for each of the plurality of brain parcels that are predicted to be relevant to the medical condition, wherein the plurality of brain parcels that are predicted to be relevant to the medical condition have been identified by operations comprising:
training a machine learning model to process an input derived from brain data for a brain of an input patient to predict whether the input patient has the medical condition; and
identifying the plurality of brain parcels that are predicted to be relevant to the medical condition using the machine learning model; and
wherein identifying the plurality of brain parcels that are predicted to be relevant to the medical condition using the machine learning model comprises:
determining, for each brain parcel in a parcel atlas, a respective importance score for the brain parcel that measures an impact of the brain parcel on predictions generated by the machine learning model; and
identifying the plurality of brain parcels that are predicted to be relevant to the medical condition using the importance scores for the brain parcels in the parcel atlas.

14. One or more non-transitory computer storage media storing instructions that when executed by one or more computers cause the one or more computers to perform operations comprising:
receiving brain data for a brain of a patient;
processing the brain data to determine a plurality of brain parcels that are predicted to be relevant to a medical condition;
determining, for each of the plurality of brain parcels that are predicted to be relevant to the medical condition, a respective brain network affiliation; and
providing, to a user device of a user, data for displaying a visualization that includes one or more respective brain network affiliations determined for each of the plurality of brain parcels that are predicted to be relevant to the medical condition, wherein the plurality of brain parcels that are predicted to be relevant to the medical condition have been identified by operations comprising:
training a machine learning model to process an input derived from brain data for a brain of an input patient to predict whether the input patient has the medical condition; and
identifying the plurality of brain parcels that are predicted to be relevant to the medical condition using the machine learning model; and
wherein identifying the plurality of brain parcels that are predicted to be relevant to the medical condition using the machine learning model comprises:
determining, for each brain parcel in a parcel atlas, a respective importance score for the brain parcel that measures an impact of the brain parcel on predictions generated by the machine learning model; and
identifying the plurality of brain parcels that are predicted to be relevant to the medical condition using the importance scores for the brain parcels in the parcel atlas.

* * * * *